United States Patent
Powers et al.

(10) Patent No.: US 9,395,264 B2
(45) Date of Patent: Jul. 19, 2016

(54) BLUNT IMPACT TEST APPARATUS AND METHOD

(75) Inventors: Donald E. Powers, Federal Way, WA (US); Mark E. Miller, Des Moines, WA (US); Jason C. Kiiskila, Kent, WA (US)

(73) Assignee: THE BOEING COMPANY, Chicago, IL (US)

( * ) Notice: Subject to any disclaimer, the term of this patent is extended or adjusted under 35 U.S.C. 154(b) by 784 days.

(21) Appl. No.: 13/160,073

(22) Filed: Jun. 14, 2011

(65) Prior Publication Data

US 2012/0318039 A1 Dec. 20, 2012

(51) Int. Cl.
*G01M 7/00* (2006.01)
*G01M 7/08* (2006.01)
*G01N 3/30* (2006.01)

(52) U.S. Cl.
CPC ... *G01M 7/08* (2013.01); *G01N 3/30* (2013.01)

(58) Field of Classification Search
CPC ............. B60R 21/0136; A61B 5/4836; A61B 19/5212; B22F 2998/00; G01L 5/00; G06F 3/0482; G06F 17/5009; G06Q 50/06; A61F 2/915; G05B 15/02
USPC .................. 73/12.01, 8, 865, 9, 865.3, 12.09
See application file for complete search history.

(56) References Cited

U.S. PATENT DOCUMENTS

| | | | | |
|---|---|---|---|---|
| 1,583,109 A * | 5/1926 | Banschbach | ................. | 73/11.04 |
| 2,200,028 A * | 5/1940 | Kudo | ........................... | 73/12.08 |
| 4,116,041 A | 9/1978 | Tholen et al. | | |
| 4,545,236 A * | 10/1985 | Turczyn | ....................... | 73/12.04 |
| 4,635,735 A * | 1/1987 | Crownover | ..................... | 175/48 |
| 5,623,094 A * | 4/1997 | Song et al. | .................... | 73/12.07 |
| 5,929,316 A * | 7/1999 | Lee | ............... | 73/12.09 |
| 7,222,515 B2 * | 5/2007 | Hatanaka et al. | ............ | 73/12.14 |
| 8,511,139 B2 * | 8/2013 | Lane et al. | ................... | 73/12.13 |
| 2003/0089167 A1 * | 5/2003 | Markstaller et al. | ............ | 73/147 |
| 2004/0230394 A1 * | 11/2004 | Saari et al. | ..................... | 702/113 |
| 2006/0005606 A1 * | 1/2006 | Hatanaka et al. | ............ | 73/12.14 |
| 2007/0044581 A1 * | 3/2007 | Wilcox et al. | ................ | 73/865.9 |
| 2010/0036565 A1 * | 2/2010 | Bernzen et al. | .................. | 701/45 |
| 2011/0035162 A1 * | 2/2011 | Matlschweiger | ............... | 702/41 |
| 2011/0313670 A1 * | 12/2011 | DeGreeve et al. | ............. | 702/13 |
| 2012/0216596 A1 * | 8/2012 | Lane et al. | ................... | 73/12.13 |

FOREIGN PATENT DOCUMENTS

| | | |
|---|---|---|
| CN | 201653673 | 11/2010 |
| CN | 201653673 U * | 11/2010 |
| CN | 201772987 | 3/2011 |
| DE | 1248333 | 8/1967 |
| DE | 2737099 | 2/1978 |

(Continued)

OTHER PUBLICATIONS http://www.microteklabs.com.

(Continued)

*Primary Examiner* — Eric S McCall
*Assistant Examiner* — Mohammed E Keramet-Amircola
(74) *Attorney, Agent, or Firm* — Hanley, Flight & Zimmerman, LLC

(57) ABSTRACT

A blunt impact test apparatus includes an apparatus frame having track rails for positioning proximate the test structure; a track angle positioning mechanism engaging the track rails to control a slope of the track rails; and an impact cart adapted to roll on the track rails.

23 Claims, 4 Drawing Sheets

(56) References Cited

FOREIGN PATENT DOCUMENTS

| | | |
|---|---|---|
| DE | 214928 | 10/1984 |
| JP | S50011641 | 5/1975 |
| JP | S56122928 | 9/1981 |
| JP | H04028615 | 1/1992 |
| JP | 2001242036 | 9/2001 |
| JP | 2002296165 | 10/2002 |
| JP | 2008286679 | 11/2008 |
| JP | S50011641 | 8/2012 |

OTHER PUBLICATIONS

Air Force SBIR/STTR Innovation, SBIR Topic #AF04-133,RX2008-127.

European Patent Office, Extended European Search Report, issued in connection with European application serial No. 12172089, issued Sep. 27, 2012, 6 pages.

State Intellectual Property Office of the People's Republic of China, English version of Notification of First Office Action, issued in connection with Chinese Patent Application No. 201210174180.6, issued on May 28, 2015, 17 pages.

Canadian Intellectual Property Office, Office Action, issued in connection with Canadian Patent Application No. 2,778,574, issued on Aug. 19, 2013, 4 pages.

European Patent Office, Communication pursuant to Article 94(3) EPC, issued in connection with European Patent Application No. 12172089.0, issued on Aug. 27, 2013, 5 pages.

Japanese Patent Office, English version of Notice of Reasons for Rejection, issued in connection with Japanese Patent Application No. 2012-124056, issued on Feb. 23, 2016 (7 pages).

State Intellectual Property Office of the People's Republic of China, English version of Notification of Second Office Action, issued in connection with Chinese Patent Application No. 201210174180.6, on Feb. 2, 2016 (13 pages).

\* cited by examiner

BLUNT IMPACT TEST APPARATUS AND METHOD

TECHNICAL FIELD

The disclosure generally relates to testing of blunt impact forces on composite materials. More particularly, the disclosure relates to a blunt impact test apparatus and method which can be used to test the effect of blunt impact having a measured magnitude on composite materials.

BACKGROUND

Aircraft and other structures built of composite materials may be inadvertently impacted by a service vehicle or other object without any external indications of the impact. Assessment of blunt impact to a composite material structure may be necessary or desirable to determine the necessity or feasibility of making repairs to the structure. Therefore, various methods used to assess the effect of blunt impact on a composite material structure have been devised.

Some techniques which have been used to assess the effect of blunt impact on composite material structures include the use of drop tubes, spring-actuated "guns" and pendulums. Drop tubes include relatively small masses (typically <100 pounds) which are dropped vertically through a tube onto a horizontal surface from a height which produces the desired energy level at impact. Spring-actuated guns use a spring to accelerate a small mass against a surface and can be used in any orientation. However, both of these techniques are limited to a small impact area (typically <~12 square inches). Pendulums use larger masses and are used to perform impacts on vertical surfaces.

A drawback of conventional drop tubes and gun-type impact devices is that their relatively small masses and relatively high velocities do not replicate the damage which is sustained from large masses at relatively low velocities. Additionally, use of such devices may render acquisition of data during the impact difficult. Pendulums are generally much lower in mass than the vehicles that cause the impact which they attempt to replicate and typically cannot be used to reliably simulate impacts low on the body of an aircraft fuselage (particularly when an attempt is made to simulate a vehicle scraping under the belly or the cargo door of an aircraft). Pendulums may also require large or tall support structures; therefore, secondary impacts caused by such structures may be difficult if not impossible to prevent.

Using any of these conventional impact simulation methods on a complete aircraft in such a manner that the aircraft mass and moments of inertia are valid would be difficult at best. As an alternative, an actual service vehicle (or other powered vehicle with the appropriate bumper shape attached to it) may be used to impact the structure but such a solution would require that a human operator control the vehicle's velocity, direction and angle of impact, which would be unsafe and have poor repeatability. Elimination of the human operator factor in such a scenario would require a complex and expensive electronic control system or external thrust system.

Accordingly, a blunt impact test apparatus and method which can be used to test the effect of blunt impact having a measured magnitude on composite materials is needed.

SUMMARY

The disclosure is generally directed to a blunt impact test apparatus for testing blunt impact against a test structure. An illustrative embodiment of the apparatus includes an apparatus frame having track rails for positioning proximate the test structure; a track angle positioning mechanism engaging the distal end of the track rails to control a slope of the track rails; and an impact cart adapted to roll on the track rails.

The disclosure is further generally directed to a method of testing a structure for survivability after impact. An illustrative embodiment of the method includes providing a test structure for testing; providing an inclined ramp placed distal to and coupled to a level ramp placed proximate to the test structure; placing a cart on the ramp, the cart configured to roll on the ramp; and rolling the cart down the ramp against the test structure.

The disclosure is further generally directed to a method of predicting the effect of impact of a service vehicle on a composite aircraft structure. An illustrative embodiment of the method includes providing a test structure for testing; providing a level ramp placed proximate to the test structure coupled to an inclined ramp placed distal and coupled to the level ramp; placing a cart on the ramp, the cart configured to roll on the ramp; and rolling the cart down the ramp against the test structure.

BRIEF DESCRIPTION OF THE ILLUSTRATIONS

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
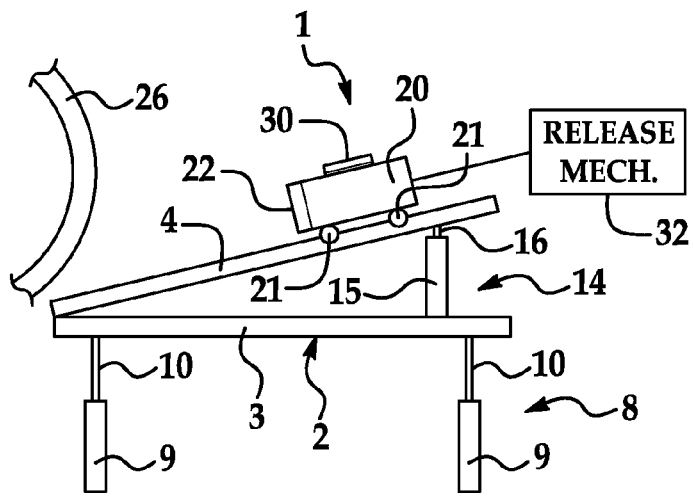
FIG. 1 is a side view of an illustrative embodiment of the blunt impact test apparatus.
Figure 2:
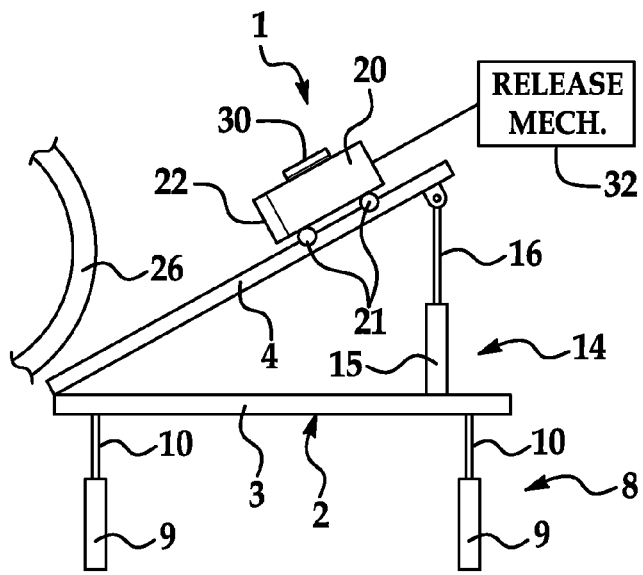
FIG. 2 is a side view of an illustrative embodiment of the blunt impact test apparatus, with a track angle positioning mechanism deployed in a raised configuration to increase the angle of the track rails.
Figure 3:
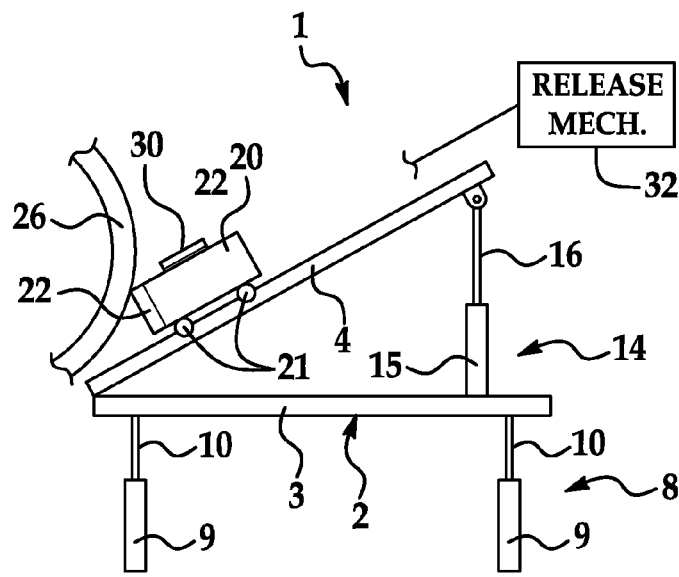
FIG. 3 is a side view of an illustrative embodiment of the blunt impact test apparatus, with the impact cart released from the cart release mechanism and an impact bumper on the impact cart impacting a test structure for testing.

Referring initially to FIGS. 1-3, an illustrative embodiment of the blunt impact test apparatus, hereinafter apparatus, is generally indicated by reference numeral 1. The apparatus 1 may include an apparatus frame 2. In some embodiments, the apparatus frame 2 may include a frame base 3 and a pair of track rails 4 provided on the frame base 3. The track rails 4 may be adjustable at an angle with respect to the frame base 3. Accordingly, a track angle positioning mechanism 14 may engage the track rails 4 for the purpose. In some embodiments, the track angle positioning mechanism 14 may include a track angle positioning cylinder 15 on the frame base 3 and a track angle positioning piston 16 which is extendable from the track angle positioning cylinder 15 and engages the track rails 4. Therefore, the angle of the track rails 4 relative to the frame base 3 may be controlled by extension or retraction of the piston 16 relative to the cylinder 15. In other embodiments, the track angle positioning mechanism 14 may be any other type of mechanism which can be used to selectively vary the angle of the track rails 4 relative to the frame base 3.

In some embodiments, a second pair of track rails (not shown) may be attached to the track rails 4, respectively, at the lower end of the track rails 4. The second pair of track rails may be generally level or horizontal and disposed adjacent to a test structure 26.

In some embodiments, a frame lifting mechanism 8 may engage the frame base 3 of the apparatus frame 2. In some embodiments, the frame lifting mechanism 8 may include at least one frame lifting cylinder 9 and a frame lifting piston 10 which is extendable from the frame lifting cylinder 9 and engages the frame base 3. Accordingly, the height or vertical position of the apparatus frame 2 can be selectively controlled by extension or retraction of the pistons 10 relative to the respective cylinders 9. In other embodiments, the frame lifting mechanism 8 may be any other mechanism which can be used to selectively raise and lower the apparatus frame 2. In still other embodiments, the frame itself can be placed atop sub-frames (not shown) which may have a fixed height to achieve the required height of the track.

Figure 1A:
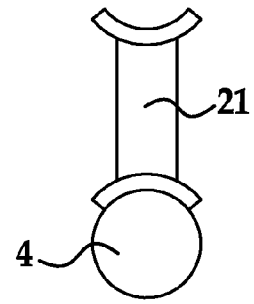
FIG. 1A is a cross-sectional view of a track rail of an illustrative embodiment of the blunt test apparatus, with an impact cart wheel engaging the track rail.

An impact cart 20 may be provided on the track rails 4 of the apparatus frame 2. The impact cart 20 may include multiple cart wheels 21 which engage the track rails 4. As shown in FIG. 1A, in some embodiments, each of the track rails 4 may be generally circular in cross-section. Each cart wheel 21 of the impact cart 20 may have a grooved or concave contour to complement the cylindrical shape of each track rail 4. Accordingly, the impact cart 20 may be adapted to roll on the track rails 4 of the apparatus frame 2 from the pre-release position shown in FIG. 2 to the impact position shown in FIG. 3 for purposes which will be hereinafter described.

A release mechanism 32 may be adapted to engage the impact cart 20 and hold or secure the impact cart 20 in the pre-release position shown in FIG. 2. The release mechanism 32 may have any design which is suitable for the purpose. In some embodiments, the release mechanism 32 may be a hydraulically-actuated release mechanism.

As further shown in FIGS. 1-3, the impact cart 20 may be adapted to receive one or multiple weight plates 30. The weight plates 30 may be added to the impact cart 20 to select the weight of the impact cart 20 for impact testing as will be hereinafter further described. In some embodiments, a sufficient number of the weight plates 30 may be added to the impact cart 20 to achieve a weight of up to 11,000 pounds or more for the impact cart 20.

An impact bumper 22 may be attached to the front of the impact cart 20. The impact bumper 22 may have any design which allows variation of (1) bumper width (can be greater than the width of the mass and track); (2) angle of impact with respect to the longitudinal axis of a test structure 26 such as an aircraft (can impact normal to the surface or obliquely); and (3) orientation with respect to the circumference of the test structure 26 such as an aircraft (can be horizontal, vertical or any given angle with respect to the structure being impacted).

In application, the apparatus 1 is placed adjacent to a test structure 26 which is to be tested. In some applications, the test structure 26 may be an aircraft. The impact cart 20 is raised to a selected height or position on the track rails 4 of the apparatus frame 2. The pre-release position (FIG. 2) of the impact cart 20 on the track rails 4 may be selected depending on the desired velocity of the impact cart 20 against the test structure 26. The frame lifting mechanism 8 can be operated to adjust the vertical position of the apparatus frame 2 and thus, the vertical position of the point of impact of the impact cart 20 against the test structure 26. The track angle positioning mechanism 14 can be operated to adjust the angle or slope of the track rails 4 in order to achieve a desired impact speed of the impact cart 20 on the track rails 4. A mechanism (not shown) to prevent multiple impacts may be installed which restrains the cart after rebounding from the initial impact with the structure under test.

The impact cart 20 is raised to the pre-release position on the track rails 4 and attached to the release mechanism 32. A selected number of weight plates 30 may be placed on the impact cart 20 to achieve a desired weight of the impact cart 20. An impact bumper 22 of selected configuration and design can be attached to the front of the impact cart 20. In some embodiments, the apparatus 1 may be used to determine the impact which would be created in the event that an aircraft service vehicle inadvertently strikes an aircraft. Therefore, the height of the apparatus frame 2, the slope of the track rails 4, the position of the impact cart 20 on the track rails 4 and the weight of the impact cart 20 may be adjusted to strike the test structure 26 at a kinetic energy level which replicates the impact kinetic energy level of the aircraft service vehicle against the aircraft.

The release mechanism 32 is operated to release the impact cart 20 such that the impact cart 20 rolls down the track rails 4 from the pre-release position shown in FIG. 2 to the impact position shown in FIG. 3 under the influence of gravity. Accordingly, the impact bumper 22 on the front of the impact cart 20 strikes the test structure 26 and may damage the test structure 26. The test structure 26 may be examined using conventional methods to determine the extent of damage to the test structure 26. The extent of damage to the test structure may be correlated to the extent of damage which would be exerted on an aircraft in the event that an aircraft service vehicle inadvertently strikes the aircraft. Accordingly, the apparatus 1 may enable electronic data acquisition of impact loads in multiple axes, acceleration, displacement and velocity of the impact cart 20 throughout the duration of the impact testing.

Figure 4:
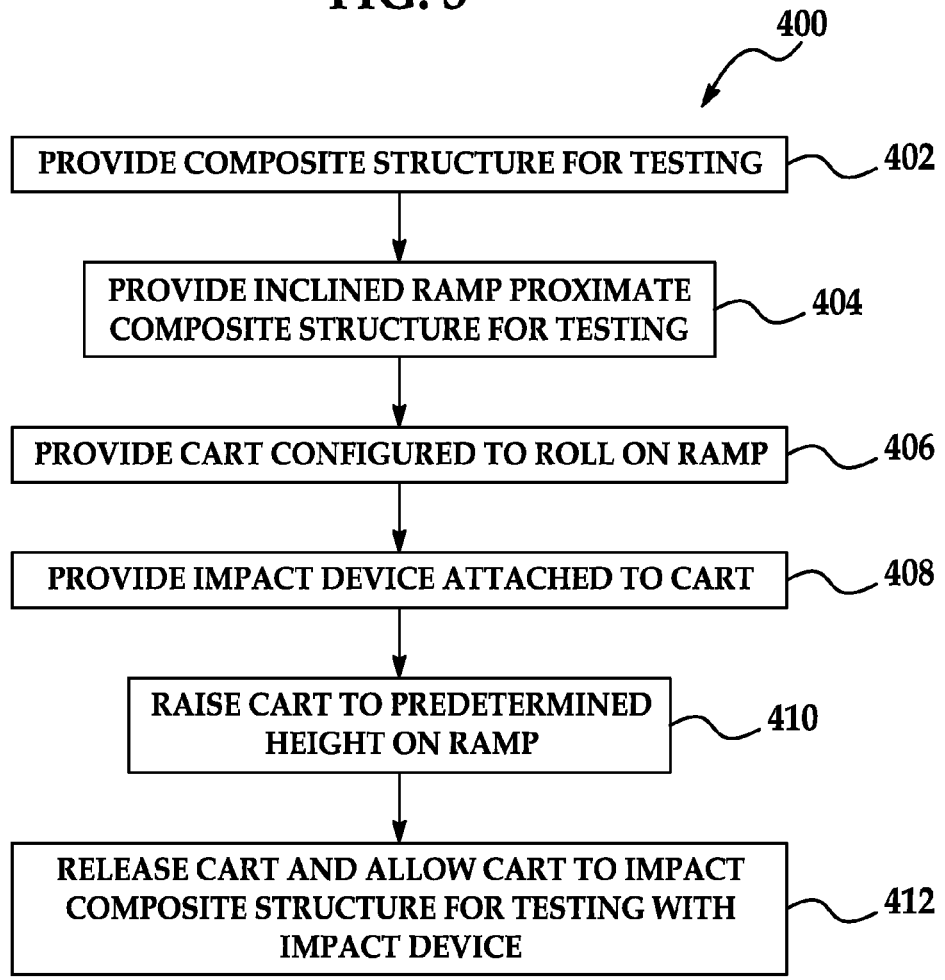
FIG. 4 is a flow diagram which illustrates an illustrative embodiment of a method of testing a structure for survivability after impact.

Referring next to FIG. 4, a flow diagram 400 which illustrates an illustrative embodiment of a method of testing a structure for survivability after impact is shown. In block 402, a composite test structure for testing is provided. In block 404, an inclined ramp is placed proximate to the composite structure for testing. In block 406, a cart which is configured to roll on the ramp is placed on the ramp. In block 408, an impact device is attached to the cart. In block 410, the cart is raised to a predetermined height on the ramp. In block 412, the cart is released and allowed to impact the test structure for impact testing.

Figure 5:
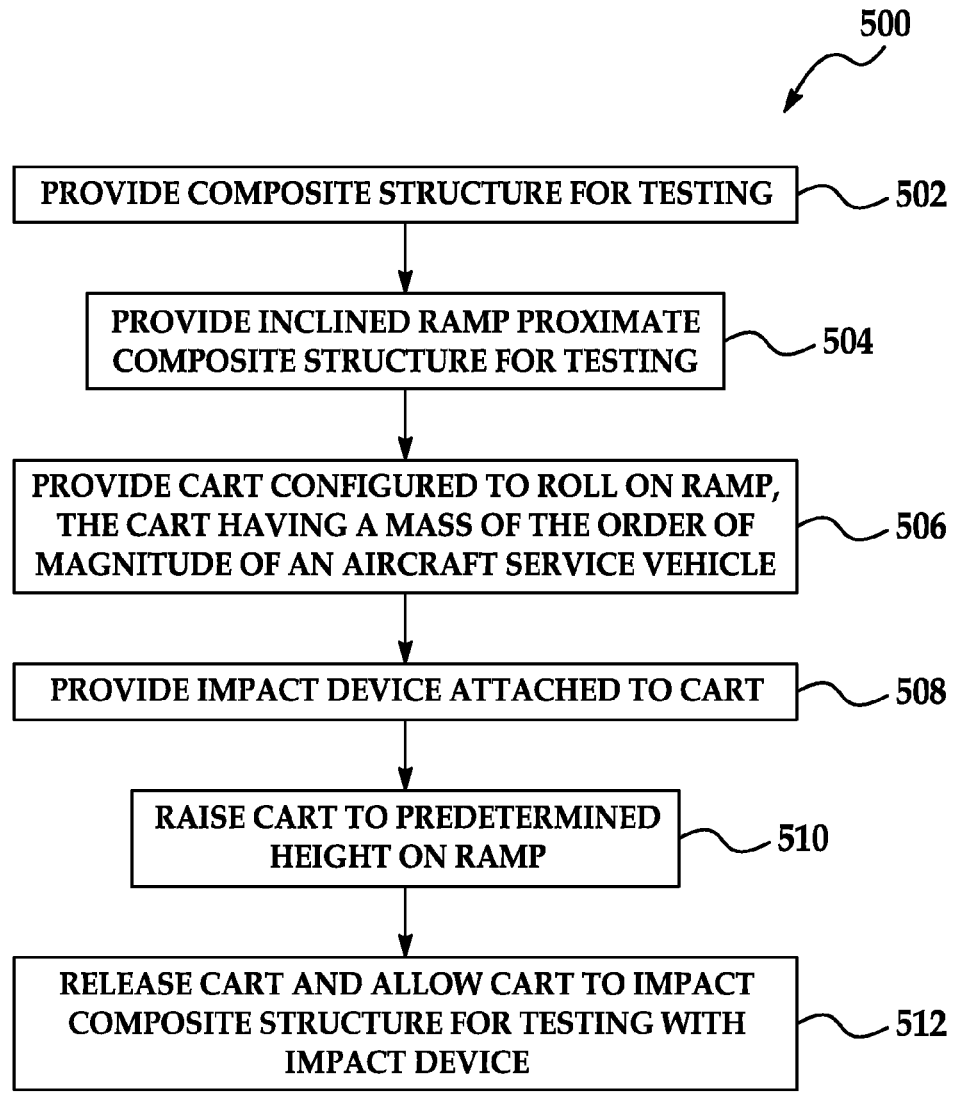
FIG. 5 is a flow diagram which illustrates an illustrative embodiment of a method of predicting the effect of impact of a service vehicle on a composite aircraft structure.

Referring next to FIG. 5, a flow diagram 500 which illustrates an illustrative embodiment of a method of predicting the effect of impact of a service vehicle on a composite aircraft structure is shown. In block 502, a composite test structure for testing is provided. In block 504, an inclined ramp is placed proximate to the composite structure for testing. In block 506, a cart which is configured to roll on the ramp is placed on the ramp. In some embodiments, the cart may have a mass of the order of magnitude of an aircraft service vehicle. In block 508, an impact device is attached to the cart. In block 510, the cart is raised to a predetermined height on the ramp. In block 512, the cart is released and allowed to impact the test structure for impact testing.

Figure 6:
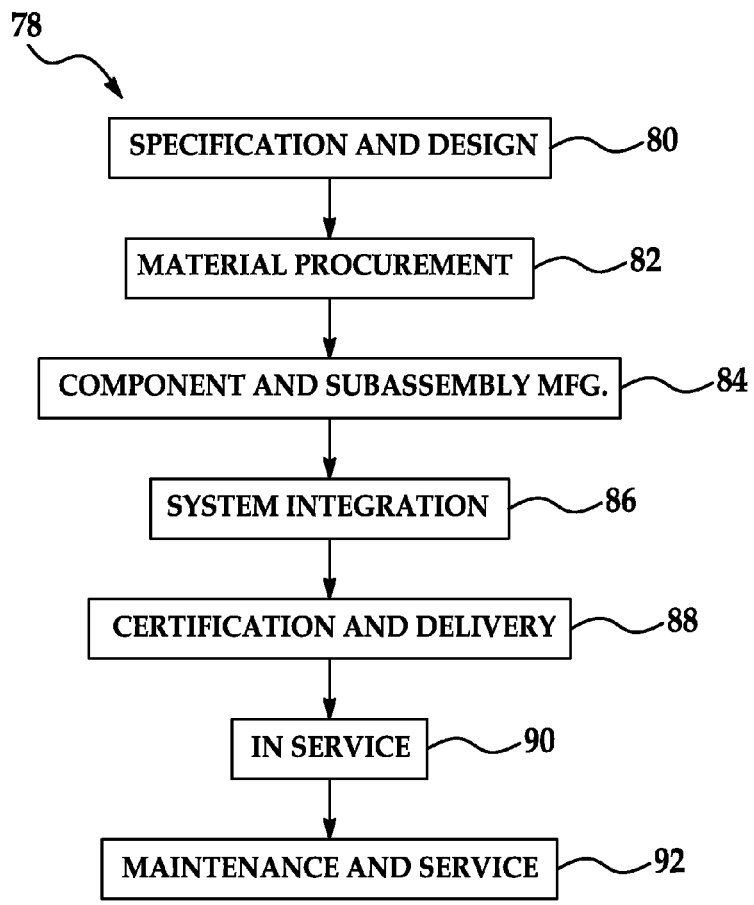
FIG. 6 is a flow diagram of an aircraft production and service methodology.
Figure 7:
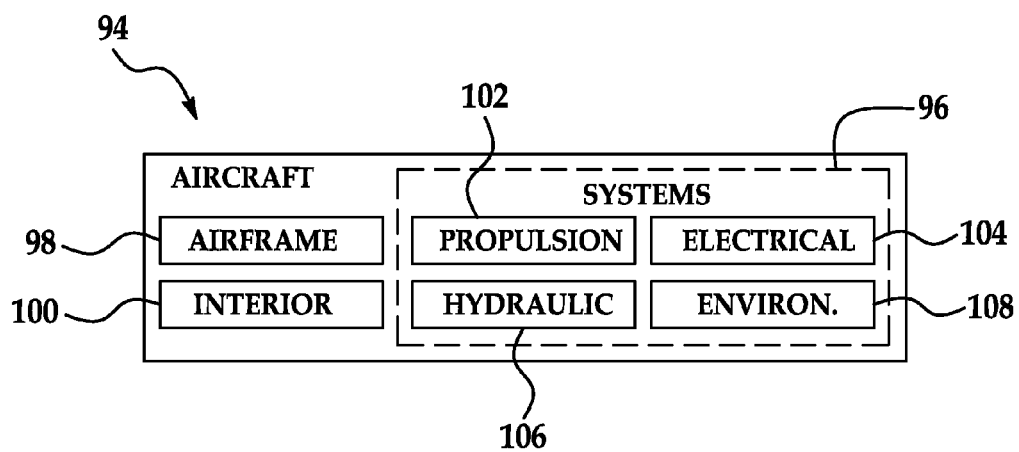
FIG. 7 is a block diagram of an aircraft.

Referring next to FIGS. 6 and 7, embodiments of the disclosure may be used in the context of an aircraft manufacturing and service method 78 as shown in FIG. 6 and an aircraft 94 as shown in FIG. 7. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 7, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A blunt impact test apparatus for testing blunt impact against a test structure, comprising:
   an apparatus frame having track rails for positioning proximate the test structure, the track rails to define a travel path to guide an impact cart comprising an adjustable impact bumper, wherein an orientation of the impact bumper is adjustable based on a circumference of the test structure, and wheels to roll the cart toward the test structure under the influence of gravity; and
   a track angle positioning mechanism engaging said track rails to control a slope of said track rails.

2. The apparatus of claim 1 wherein the wheels are grooved cart wheels and said track rails are cylindrical along a direction of the travel path and are configured to guide the grooved cart wheels of the impact cart when the grooved cart wheels are engaging said track rails.

3. The apparatus of claim 1 wherein said track angle positioning mechanism comprises a hydraulic cylinder and a piston extending from said hydraulic cylinder.

4. The apparatus of claim 1 further comprising a release mechanism to hold the impact cart in an elevated position and to release the impact cart to enable the impact cart to roll along the track rails.

5. The apparatus of claim 1 wherein the impact cart rolls toward the test structure at an initial velocity greater than zero.

6. The apparatus of claim 1, wherein the adjustable impact bumper is further adjustable to vary one or more of a width of the adjustable impact bumper, or an angle of impact of the adjustable impact bumper relative to the test structure.

7. The apparatus of claim 1 further comprising a frame lifting mechanism to engage said apparatus frame to adjust a height of the apparatus frame.

8. The apparatus of claim 7 wherein said frame lifting mechanism comprises a hydraulic cylinder and a piston extending from said hydraulic cylinder.

9. A method of testing a structure for survivability after impact, comprising:
   providing a test structure to be tested;
   placing an inclined ramp proximate to said test structure;
   adjusting an angle of the inclined ramp based on a kinetic energy to be provided to said test structure by defining a travel path to guide a cart, wherein the cart comprises wheels for rolling and an adjustable impact bumper, wherein an orientation of the impact bumper is adjustable based on a circumference of the test structure;
   placing said cart on said ramp; and
   rolling said cart down said ramp to cause the cart to impact said test structure under the influence of gravity.

10. The method of claim 9 further comprising raising said cart to a predetermined height on said ramp.

11. The method of claim 9 further comprising placing at least one weight plate on said cart.

12. The method of claim 9 wherein rolling said cart down said ramp is to cause the cart to impact said test structure with the adjustable impact bumper.

13. The method of claim 9 wherein rolling the cart down the ramp comprises providing an initial velocity to the cart, the initial velocity greater than zero.

14. The method of claim 9, wherein the adjustable impact bumper is further adjustable to vary one or more of a width of the adjustable impact bumper, or an angle of impact of the adjustable impact bumper relative to the test structure.

15. The method of claim 9 wherein the test structure comprises an aircraft.

16. The method of claim 15 wherein said cart has a mass of the order of magnitude of an aircraft service vehicle when the cart impacts the test structure.

17. A method of testing a structure for survivability of an impact, comprising:
   providing a test structure to be tested;
   placing a ramp proximate to said test structure to define a travel path of a cart, wherein the cart comprises wheels for rolling and an adjustable impact bumper;
   adjusting an incline of said ramp based on a desired impact of the cart on said test structure;

adjusting an orientation of the adjustable impact bumper based on a circumference of the test structure; and rolling said cart down said ramp to cause said cart to impact said test structure, the cart to roll under the influence of gravity.

18. The method of claim 17 further comprising raising said cart to a predetermined height on said ramp.

19. The method of claim 17 further comprising adding mass to the cart after placing said cart on said ramp.

20. The method of claim 17 wherein rolling said cart down said ramp is to cause the cart to impact said test structure with the adjustable impact bumper.

21. The method of claim 17 wherein rolling the cart down the ramp comprises providing an initial velocity to the cart, the initial velocity greater than zero.

22. The method of claim 17, wherein the adjustable impact bumper is further adjustable to vary one or more of a width of the adjustable impact bumper, or an angle of impact of the adjustable impact bumper relative to the test structure.

23. A blunt impact test apparatus for testing blunt impact against a test structure, comprising:

an apparatus frame having track rails for positioning proximate the test structure, the track rails to define a travel path to guide an impact cart comprising wheels to roll the cart toward the test structure under the influence of gravity and an adjustable impact bumper, wherein the wheels are grooved cart wheels and the track rails are cylindrical along a direction of the travel path and are configured to guide the grooved cart wheels of the impact cart when the grooved cart wheels are engaging the track rails, and wherein the adjustable impact bumper is adjustable to vary a width of the adjustable impact bumper, an angle of impact of the adjustable impact bumper relative to a longitudinal axis of the test structure, and an orientation of the adjustable impact bumper with respect to a circumference of the test structure; and a track angle positioning mechanism engaging the track rails to control a slope of the track rails.

* * * * *